United States Patent [19]

Kristoufek

[11] Patent Number: 4,710,300

[45] Date of Patent: Dec. 1, 1987

[54] METHOD FOR PROCESSING OF ORGANIC MATERIALS CONTAINING NITROGEN COMPOUNDS

[75] Inventor: Jaroslav Kristoufek, Prague, Czechoslovakia

[73] Assignee: Ceskoslovenska akademie ved, Prague, Czechoslovakia

[21] Appl. No.: 491,980

[22] Filed: May 5, 1983

Related U.S. Application Data

[63] Continuation of Ser. No. 269,710, Jun. 2, 1981, abandoned, which is a continuation-in-part of Ser. No. 119,142, Feb. 5, 1980, abandoned.

[30] Foreign Application Priority Data

Oct. 29, 1976 [CS] Czechoslovakia ............... 6994-76

[51] Int. Cl.$^3$ ........................... C02F 3/28; C02F 1/04
[52] U.S. Cl. ........................... 210/603; 210/631; 210/180; 210/182; 71/10; 71/12; 203/23; 203/36
[58] Field of Search ............. 210/603, 605, 631, 903, 210/197, 198, 199-202, 180, 182; 48/197 A; 71/10, 12; 203/23, 33, 36, 37

[56] References Cited

U.S. PATENT DOCUMENTS

| | | | |
|---|---|---|---|
| 3,278,423 | 10/1966 | Millar | 203/36 |
| 4,104,131 | 8/1978 | Didycz et al. | 203/36 |
| 4,134,830 | 1/1979 | Skogman et al. | 210/903 |
| 4,137,158 | 1/1979 | Ishida et al. | 210/605 |
| 4,140,586 | 2/1979 | Kwasnoski et al. | 203/10 |
| 4,162,153 | 7/1979 | Spector | 210/903 |

FOREIGN PATENT DOCUMENTS 50-144267  11/1975  Japan .................. 210/903

Primary Examiner—Benoit Castel

[57] ABSTRACT

The invention pertains to a method for processing of organic materials containing nitrogen compounds, where the organic material undergoes an anaerobic digestion with simultaneous liberation of biogas which contains methane and carbon dioxide. The liquid product obtained after anaerobic digestion is, according to the invention, heated to boiling temperature, ammonia bonded as carbonate which is distilled off, and the tail product from distillation is further processed to the valuable product and clear water or is discharged as prepurified waste water. During the processing to the valuable product in the form of organo-phophate-lime concentrate, the tail product of distillation is alkalized by lime and carbonized with carbon dioxide. Biogas or carbon dioxide obtained by distillation may be used in carbonation. The processed organic materials may be excrements from farming of hogs and black cattle, waste from chemical and alimentary industry, city sewage sludges, and various kinds of biomass which may be employed in the process of anaerobic digestion for production of biogas.

7 Claims, 3 Drawing Figures

METHOD FOR PROCESSING OF ORGANIC MATERIALS CONTAINING NITROGEN COMPOUNDS

This is a continuation of application Ser. No. 269,710 filed June 2, 1981, which is a continuation-in-part of Ser. No. 119,142 filed Feb. 5, 1980, both now abandoned.

BACKGROUND OF THE INVENTION

The invention pertains to the method and equipment for processing of organic materials containing nitrogen compounds, which consists in an anaerobic digestion of the organic material under liberation of biogas containing methane and carbon dioxide.

"Organic materials" means, in the present description, excrements of hogs and black cattle, waste from alimentary and chemical industry, city sewage sludges and various kinds of biomass which may be employed in the process of anaerobic digestion to obtain biogas.

Several methods have been recently employed in the processing technology of the above-mentioned organic materials. Some of them are only intended as a suitable physical or mechanical treatment, e.g. dewatering or drying to the form of fertilizer or a raw material for further processing. The composition of organic materials does not substantially change during such treatment. A part of the treatment sometimes includes the step of processing by heat, the purpose of which is to destroy harmful microorganisms, see German Patent Application(DOS) 520,287 and British Pat. No. 1,492,396.

Biological aerobic oxidation is also used in the liquification of these organic materials which is realized by means of several technological variants. The common problem of these technologies of the state of the art is that the valuable components and potential energy present in the processed organic material are not fully utilized; high start-up costs and operation expenses; and the sensitivity of the biological process to external influences. According to the German Patent Application (DOS) 2,723,906, excrements are sterilized by alkaline hydroxides prior to the aerobic oxidation to mitigate the afore-mentioned drawbacks. In addition, urea is partly transformed to ammonia and its compounds during this process. The treatment comprising aerobic oxidation has a high power consumption demand for operating the aeration equipment. Thus, 2 kWh are consumed for removal of 1 kg of the dry organic material. Another disadvantage lies in the production of very undesirable nitrates which wind up in the waste water.

Anaerobic digestion has been utilized a long time in the treatment of waste, above all in sewage plants. The process takes place in sealed heated tanks without leaking of offensive odor. Biogas containing aobut 60% $CH_4$ and 35% $CO_2$ is a byproduct and is formed in the amount of about 300–700 liters per kg of the dry organic material introduced into this process, depending on the material composition. The calorific value of gas is about 6000 kcal/$Nm^3$. U.S. Pat. No. 4,057,401 describes a method which employs an additional heating of the digestion tank by solar radiation to intensify the heating process.

A fundamental disadvantage of the purification processes by anaerobic digestion of the state of the art is the insufficient utilization of all valuable compounds present in the organic materials and the high contamination of the digested product which has to be further purified, for example, biologically. Such post purification is very difficult with animal farm waste and is realized only by mixing with city sewage water to achieve high dilution. This condition requires locating large fattening stations near large cities, which is undesirable for other reasons. Similarly, as in the aerobic purification, also in the more recent procedures using anaerobic digestion, the main part of nitrogen, which is the most valuable component of waste, is disadvantageously transferred into solution in the form of ammonia and oxidized during the subsequent biological purification to nitrates. Nitrates remain in clear water as a very harmful component.

BRIEF DESCRIPTION OF THE INVENTION

It is an object of the invention to provide a process of processing of organic materials containing nitrogen compounds having a maximum yield of valuable product, without demands to the external supplies of energy and excluding unfavorable effects to the environment.

The method of the invention produces valuable products containing concentrated, nitrogen and phosphate and clear water from a liquid product obtained after anaerobic digestion of organic compounds. Such method comprises the steps of heating the liquid product to a boiling temperature, subjecting the heated liquid product to a rectification whereby to develop a gaseous phase to produce ammonia, carbon dioxide, and water or the product formed by the chemical reaction of said compounds of the gaseous phase such as ammonium carbonate and ammonium water, and isolating the tail product of the distillation with the residual content of less than 250 mg $NH_3$ bonded as carbonate thereto per kg of the tail product to produce phosphate containing concentrate. The liquid product from the anaerobic digestion may be preheated by a heat accumulated in the tail product of the distillation. The tail product of distillation may be alkalized by an equivalent amount of lime up to 20 g CaO per 1 kg with the simultaneous draining of residual ammonia, thereafter carbonizing by carbon dioxide the alkalized product to the final value of 0.01 to 1.5 g CaO per 1 kg, and then separating in a decanter the valuable product mechanically in the form of organo-phosphato-lime concentrate and clear water.

The apparatus used in the invention comprises a digestion tank for receiving the organic materials connected by conveying means with a source of organic materials, said digestion tank having a first outlet for a biogas and a second outlet for a liquid digestion product, a rectification column having an inlet for introducing the liquid digestion product through the feed line connecting the second outlet of the digestion tank with said inlet of the column, the distillation column having at its upper end an outlet for ammonia and at its lower end a heating equipment and an outlet for a tail product of distillation, a reservoir of biogas provided with an inlet connected to the first outlet of the digestion tank and an outlet connected to the heating equipment of the column, and a device for processing the tail product to the valuable product and clear water connected to the outlet of the tail product. The device for processing the tail product may comprise a liming tank furnished with dosing equipment for liming, a carbonation tank provided with inlet and an outlet for carbonizing gas, a decanter having an outlet for a valuable product and an outlet for water, first conduit means connecting the outlet for the tail product with the liming tank, second conduit means connecting the liming tank with the carbonizing tank, and third conduit means connecting the carbonation tank with the decanter.

It is commonly known that the nitrogen is bound in excrements and sewage materials in the form of ammonium salts of carbonic acid. The present invention is based on the application of unique and specific properties of these salts. Ammonium salts are solid and crystalline at ambient temperature. However, at a temperature about 60° C. the salts are dissociated to their simple constituents $CO_2$, $NH_3$ and $H_2O$ and thereby transformed to a gaseous state.

By the cooling of such gaseous mixture the ammonium salts are again directly recomposed from their simple constituents.

The theoretical basis for that phenomenon resides in the fact that the boiling points of said constituents differ significantly from each other ($CO_2$ b.p.$=78°$ C.; $NH_3$ b.p.$=33°$ C., $H_2O=100°$ C.) This fact led the inventor to discover the possibility of the isolation of ammonium salts of carbonic acid after their dissociation even from high diluted solutions through rectification. In this way, concentrated mixtures of $NH_3$, $CO_2$ and $H_2O$ in various molar ratios can be obtained and by mere cooling, pure solid salts of the carbonic acid of the required constitution, e.g., ammonium carbonate, ammonium bicarbonate, ammonium carbamate are directly produced. Through more efficient rectification using a column with e.g. a greater number of plates and a higher reflux ratio the mixture can be divided into the constituents $CO_2$, $NH_2$ and $H_2O$. The process of the dissociation by heat of ammonium salts of carbonic acid as a starting material can be produced.

In the present invention the lime is added to the tail product of the column after distilling off the ammonia at a temperature close to 100° C. By adding the lime to the tail product no substantial reaction occurs except those with phosphate compounds since all ammonium carbonate compounds have been decomposed by heating and the ammonia and $CO_2$ have been distilled off.

The supply of lime and subsequently $CO_2$ into the hot tail product has for its result the formation of calcium carbonate of high absorption activity which contributes immediately to an increased water purification effect. The fresh calcium carbonate stimulates the formation of the precipitate of calcium carbonate and phosphate which, due to its high absorption activity, absorbs colloids, retains phosphorous, and improves the filtrability of the suspension. Favorable absorption properties of the newly formed calcium carbonate are determined by the reaction conditions which are, first of all, characterized by a high reaction temperature about 80° C. It is known e.g. from the sugar industry, that at just about this temperature calcium carbonate with high absorption activity can be prepared. The high temperature simultaneously accelerates the process of recrystallization of the sludge towards the formation of coarse-grained crystals of precipitate comprising calcium carbonate and phosphate. All of this has important positive effect in the process of water clarification, and can be envisaged as a result of the inventive combination with the step of column distillation.

A feature of the invention resides in that the liquid product, after anaerobic digestion, is heated to boiling temperature, ammonia bonded as carbonate is distilled off, and the tails of distillation are worked into a valuable product and clear water or are discharged as prepurified waste water.

Distillation may be advantageously carried out to the residual content of less than 250 mg $NH_3$ per 1 kg of distillation residue. The tail product may be, according to the invention, further alkalized by the equivalent amount of lime up to 20 g CaO per 1 kg, then carbonized with carbon dioxide to the final value 0.01 to 1.5 g CaO per 1 kg, and the formed carbonation sludge may be then mechanically separated from clear water in the form of an organic-phosphate-lime concentrate. Biogas from anaerobic digestion or carbon dioxide obtained in the distillation of ammonia from the liquid product or by combustion of biogas may be used for carbonation. The equipment for the above-said method consists of a digestion chamber equipped with an inlet piping of biomass and a piping for digested product, where the piping for digested product is fed to the inlet of a distillation column and the piping of biogas is connected through a gas reservoir and further piping to the equipment for heating of the distillation column, while the ammonia exhaust of the distillation column is connected to an equipment for ammonia processing and the outlet of the tail fraction to an equipment for processing of the tail product.

The basic advantage of the invention consists in the complete utilization of all valuable compounds and energy, which are present in organic materials containing nitrogen compounds, to obtain final products suitable as fertilizers in a concentrated form or as a fodder.

The invented process provides for a more efficient processing of the digested product after anaerobic digestion and makes possible a broad application of anaerobic digestion as an important source of energy which has been under-utilized till now due to the difficulties connected with the processing of digested products.

The process according to the invention is characterized by a high degree of removal of organic compounds and virtually complete removal of phosphorus, nitrogen and infectious micro-organisms from water resulting in the process. It combines the function of the secondary and tertiary water treatments in the sense of water technology. Concerning the utilization of solid waste, it represents a wasteless technology, because all original components of the organic material are recovered as the valuable product.

Dewatering of carbonation sludges does not require an expensive centrifugation. Common filtration methods suffice and the resulting water has a high degree of purity due to the coagulation and sterilization effects of heat and the flocculation and absorption action of lime and can be reused, e.g. in the fattening station.

Only lime has to be supplied into the process, but it is transferred into final valuable products. Carbon dioxide for carbonation is at disposal in the form of by-produced biogas or as the gaseous product of distillation. The process has low energy demands and the whole energy consumption may be covered by combustion of by-produced boigas. If the process is applied in large fattening stations, it makes possible their independent existence in any exposed region with respect to water supplies and hygiene.

BRIEF DESCRIPTION OF THE DRAWINGS

The invention is further illustrated in the appended drawings in which.

DETAILED DESCRIPTION OF THE INVENTION

Figure 1:
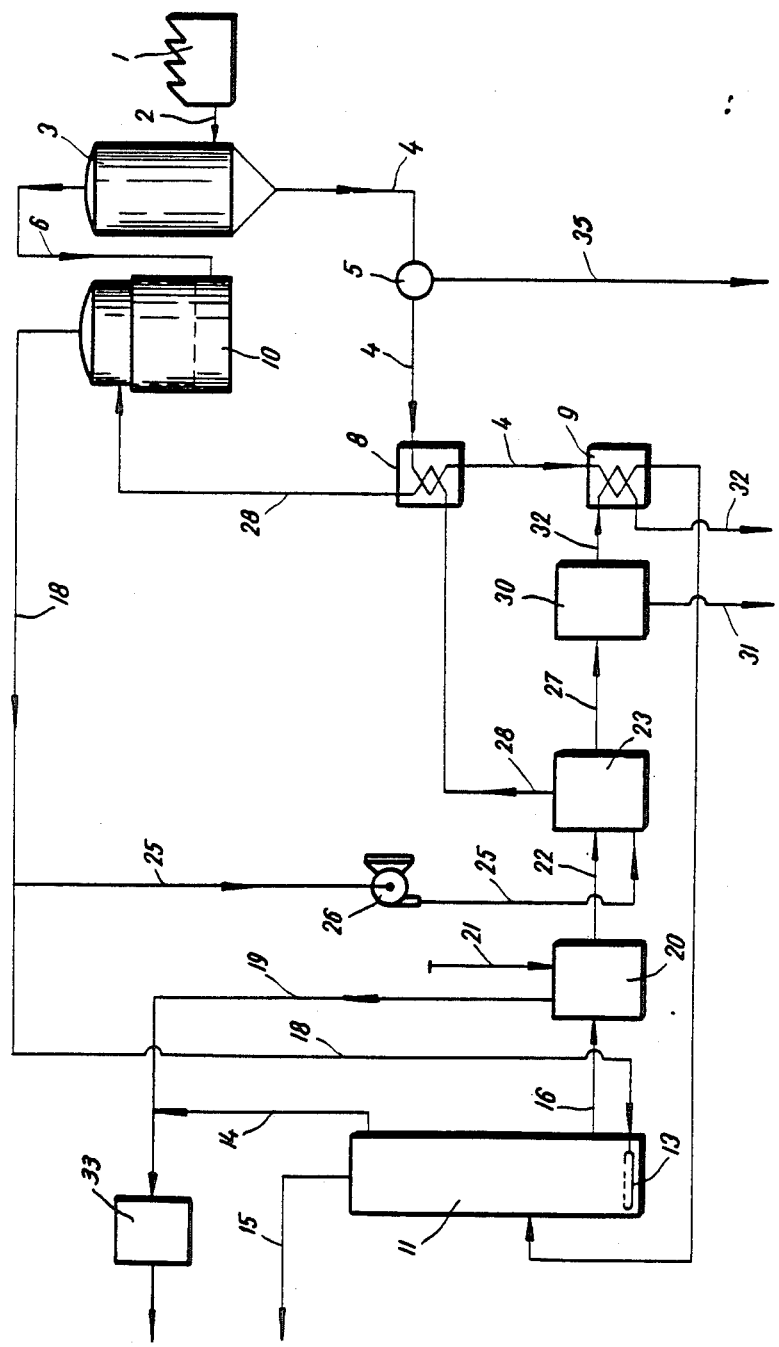
FIG. 1 illustrates the scheme of a first one of the possible variants of equipment for the method according to the invention.

Turning first to FIG. 1, source of organic material 1, e.g., a building of high-capacity cattle stables, is connected by piping 2 to the digestion chamber 3, which has the equipment for entrapping of biogas. The digestion chamber 3 has two outlet pipelines. The pipeline for digested product 4 leads through a separator 5 and heat exchangers 8, 9 to the inlet of distillation column 11. The separator 5 is furnished with an outlet pipe 35 of rough suspensions. The pipeline 6 of biogas is connected with the gas reservoir 10 and through further pipeline 18 leads to the heating equipment 13 placed at the bottom of distillation column 11. On the top end of the distillation column 11 there is attached an exhaust pipe for ammonia 14 and an exhaust pipe for carbon dioxide 15. The exhaust pipe for ammonia 14 is further connected to some of the known equipment 33 for ammonia processing. The outlet of tail product 16 of distillation column 11 is connected to the liming tank 20 provided by means for dosing of lime 21 and the exhaust pipeline of ammonia 19. The liming tank 20 is further connected by pipe 22 with the carbonation tank 23, which has also the inlet of biogas 25 and the outlet of gas 28. The biogas inlet 25 is furnished with a blower 26. The heat exchanger 8 is inserted into the gas outlet 28 which is connected to the gas reservoir 10. The carbonation tank 23 is connected by pipeline 27 with the decanter 30, which has the outlet of valuable product 31 and also the outlet of clear water 32 with the inserted heat exchanger 9.

Organic materials are transported from the source of organic digestion chamber 3, which has the equipment for entrapping of biogas. The digestion chamber 3 has two outlet pipelines. The pipeline for digested product 4 leads through a separator 5 and heat exchangers 8, 9 to the inlet of distillation column 11. The separator 5 is furnished with an outlet pipe 35 of rough suspensions. The pipeline 6 of biogas is connected with the gas reservoir 10 and through further pipeline 18 leads to the heating equipment 13 placed at the bottom of distillation column 11. The exhaust pipe for ammonia 14 is further connected to some of the known equipment for ammonia processing. The outlet of tail product 16 of distillation column 11 is connected to the liming tank 20 provided by means for dosing of lime 21 and the exhaust pipeline of ammonia 19. The liming tank 20 is further connected by pipe 22 with the carbonation tank 23, which has also the inlet of biogas 25 and the outlet of gas 28. The biogas inlet 25 is furnished with a blower 26. The heat exchanger 8 is inserted into the gas outlet 28 which is connected to the gas reservoir 10. The carbonation tank 23 is connected by pipeline 27 with the decanter 30, which has the outlet of valuable product 31 and also the outlet of clear water 32 with the inserted heat exchanger 9.

More specifically the equipment operates in the following way:

Organic materials are transported from the source of organic materials 1 through the pipeline 2 into the digestion chamber 3 where the materials 1 undergo a methane digestion under anaerobic conditions and liberate biogas which is led into the gas reservoir 10. The digestion chamber 3 is of a common design used in sewage plants. The digested product is transported into the separator 5, where rough suspensions are separated and these suspensions may be used as a fertilizer. The liquid product materials 1 through the pipeline 2 into the digestion chamber 3 where the materials 1 undergo a methane digestion under anaerobic conditions and liberate biogas which is led into the gas reservoir 10. The digestion chamber 3 is of a common design used in sewage plants. The digested product is transported into the separator 5, where rough suspensions are separated and these suspensions may be used as a fertilizer. The liquid product from the separator 5 passes through heat exchangers 8, 9 where it is preheated by gas leaving the carbonation tank 23 and by clear water, and is charged into the rectification distillation column 11 which is heated by biogas from anaerobic digestion. The liquid product is heated in the distillation column 11 to boiling temperature and a gaseous phase develops, which contains above all ammonia and carbon dioxide, and which is converted to some valuable product in known equipment which need not be further described, e.g. into concentrated ammonia water, ammonium carbonate, anhydrous ammonia, urea, etc. Carbon dioxide may be employed as carbonation gas which may be obtained from the column 11 in the processing of the liquid product from the distillation column 11 in the carbonation tank 23.

After 70% to 90% of carbonate bonded ammonia has been distilled off, heating in the distillation column 11 is interrupted and the tail product is discharged or repumped into the liming tank 20, where lime is added and further liberation of ammonia occurs. Ammonia is worked out in the same way as it is from the distillation column 11.

It is understood that the term "lime" means calcium oxide, or powdered calcium hydroxide, or calcium hydroxide in the form of lime milk. To accelerate the process, the liming tank 20 may be, if desired, furnished with heating facilities, e.g. an inlet of steam, or may be adapted as the carbonation tank at the same time. Alternatively, the liming tank 20 can be omitted and lime can be directly dosed into the lower part of distillation column 11, the construction of which is adapted for this purpose.

If the demands on the degree of water purification are lowered, the tail product from the distillation column 11 may be cooled in the heat exchanger and directly discharged as prepurified water into sewerage.

On completion of liming, the resulting alkaline tail product is carbonized in the carbonation tank 23 by biogas, which is transported under elevated pressure by the blower 26 from the gas reservoir 10. The formed precipitate of calcium carbonate and phosphate very efficiently clarifies the alkalized tail product, absorbs colloids, retains phosphorus, and improves the filtrability of suspension. The carbonation sludge formed in this way is led into the decanter 30 or into a conventional type of filtration apparatus, where water and the valuable product, i.e. the organophosphate-lime concentrate, are separated. The concentrate is used as a component of fertilizers or feeding blends.

The liquid component is water purified to a high degree, free of infections germs and with a minimum content of nitrogen and organic compounds and phosphorus. Therefore, it may be either directly reused in the operation, e.g. in the fattening station, or discharged into sewerage. The quality of the final products, including the water, depends on parameters of the applied rectification distillation column, i.e. on the number of plates and the reflux ratio, on a lime dose, and the like. However, these factors also affect the overall economy of the process and therefore are determined by means of methods commonly known with respect to the required parameters for the end products.

In the following Table I experimental data which were obtained by performing the method of the invention are set forth. The starting material for rectification distillation was a sewage water produced from the anaerobic digestion of excrements of hogs having the molar ratio $NH_3:CO_2=0.94$. Products obtained by the rectification of the following compositions were obtained: (all contents are given in % by weight):

TABLE I

| Temperature of the dephlegmator (partial condenser of the column) | Content $NH_3$ | Content $CO_2$ | Content $H_2O$ | Molar ratio $NH_3:CO_2$ |
|---|---|---|---|---|
| 60 | 39.26 | 56.15 | 4.6 | 1.81 |
| 72 | 30.78 | 55.01 | 14.21 | 1.45 |
| 80 | 22.37 | 42.63 | 35.00 | 1.36 |
| 85 | 15.12 | 29.75 | 55.08 | 1.32 |

With a temperature of 60° C. the dephlegmator, the ammonium salt obtained as a white crystalline compound by the cooling of the gaseous mixture, has the lowest content of water, and even at a temperature of 78° C., the salt can be obtained in a powdered structure. At a higher temperature of the dephlegmator, by cooling, a solution of ammonia water with carbon dioxide is produced. The absorption ability of the carbon dioxide is produced. The absorption ability of the carbon dioxide in ammonia water had a downward tendency with increased temperature, as carbon dioxide is a constituent with higher fugacity in comparison with ammonia and water.

In accordance with the present invention, final products are obtained directly in pure form as ammonium salts of carbonic acid or their concentrated individual components. The composition of the final products can be easily and extensively controlled by estabilshing various conditions of the process.

EXAMPLE 1

The starting organic material to be processed was 300 kg of liquid dung which was produced during a day by 300 stabled hogs. Dung composition:

| Water | 92% |
|---|---|
| Dry substance | 8% |
| Organic part in the dry substance | 80% |
| Total nitrogen | 6 g per 1 kg of liquid dung |
| Total phosphorus | 2 g per 1 kg of liquid dung |

The anaerobic methane digestion of liquid dung for 16 days at temperature 38.5° C. yielded 120 $Nm^3$ of biogas composed of 64% methane and 35% $CO_2$. The rough-grained humuslike product was separated in a screen separator and the residual liquid product was charged into a distillation (rectification) column of 18 plates. The distillation column operated in the atmospheric regime (atmospheric pressure in the column head). Column distillation gave 70 kg of ammonia water containing 250 g $NH_3/kg$. The heated tail product of the distillation column was alkalized in a closed reactor directly heated by steam, which had the function of liming tank and carbonator, with 12 g CaO per 1 kg of tail product. The charge of the reactor was then carbonized by biogas at temperature 80° C. to the residual alkality 0.10 g CaO/kg of tail product. The formed grainy carbonation sludge rapidly separated from liquid phase and contained calcium phosphate and carbonate which was separated in a decanter from the water, which was cooled in a heat exchanger and discharged. Carbonation sludge from the decanter was dewatered in a filter press and used as a concentrated phosphate fertilizer.

EXAMPLE 2

The starting waste to be processed according to the invention was a thickened sludge from a mechanical-biological sewage plant which purified combined sewage water from a city agglomeration and alimentary industry. The composition of thickened sludge was as follows

| Water | 93% |
|---|---|
| Dry substance | 7% |
| Organic part of dry subatance | 77% |
| Total nitrogen | 4.5 g per 1 kg of sludge |
| Total phosphorus | 1.5 g per 1 kg of sludge |

The sludge was processed in a way similar to that in Example 1. However, due to the lower content of dry substance, nitrogen and phosphorus, proportionally less by way of end products were obtained, i.e. of biogas, ammonia water and phosphate carbonation sludges. A lower amount of CaO was used for this reason, i.e. the dose of 6 g CaO per 1 kg of sludge in the alkalization of tail product from the distillation column before carbonation.

Figure 2:
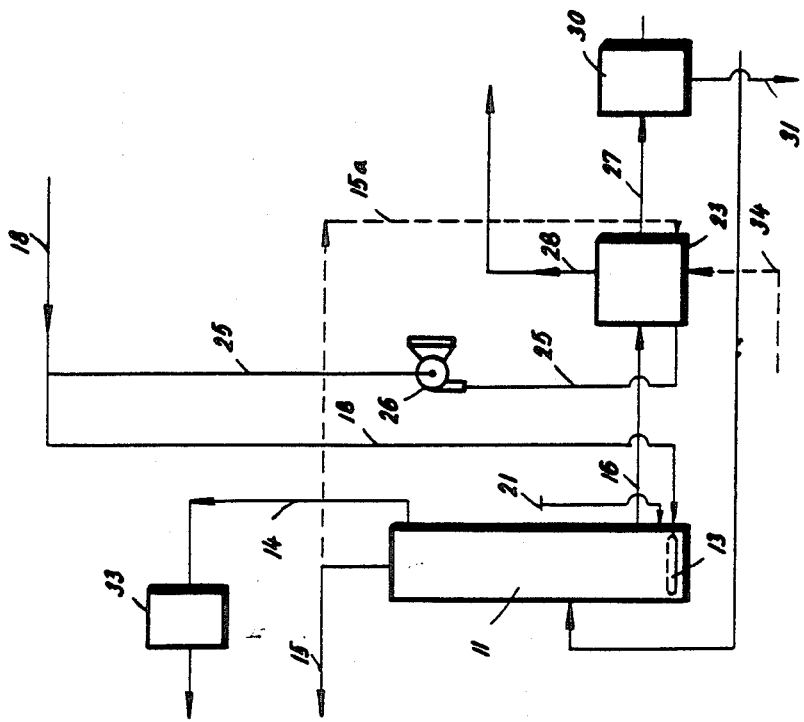
FIG. 2 is a fragmentary view illustrating a second variant of equipment according to the invention.
Figure 3:
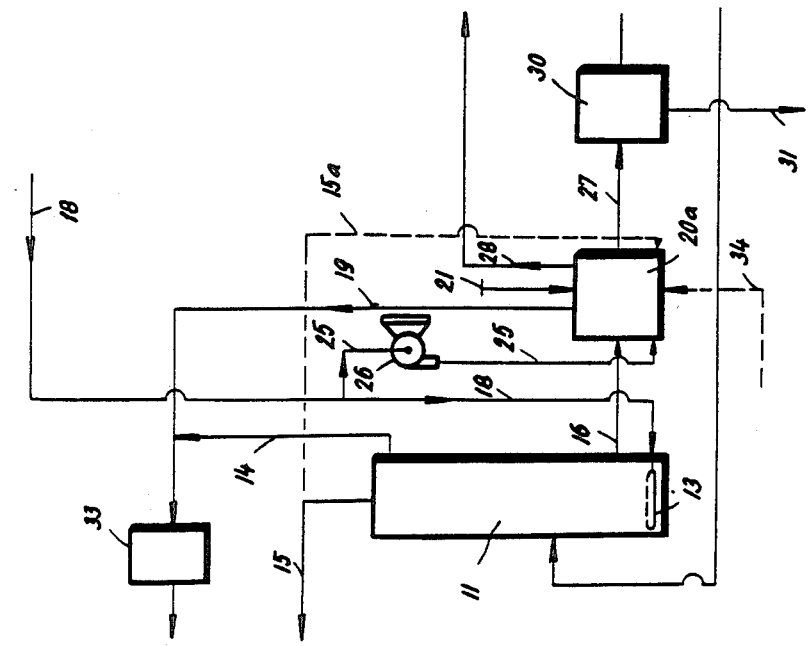
FIG. 3 is a fragmentary view illustrating a third variant of equipment according to the invention.

In FIGS. 2 and 3 there are shown, respectively, two major alternatives of the possible embodiments of the apparatus carrying out the process steps of liming and carbonizing by treating the tail produce of the distillation column.

According to the first alternative, shown in FIG. 2, the liming tank 20 and the carbonizing tank 23 are associated in one unit where both the liming and the later carbonation occur. Accordingly, this united liming-carbonation tank designated 20a is provided by the means 21 for dosing lime and the biogas inlet 25 furnished with the blower 26 and further with the pipeline 19 for exhausting ammonia and the gas outlet 28. The tail product of the distillation column 11 is thus supplied into the liming-carbonation tank 20a, i.e. precipitate of calcium carbonate and phosphate is led into the decanter 30 by the pipeline 27.

In the second alternative, shown in FIG. 3, the liming tank is omitted and the process of liming takes place directly in the distillation column 11 which is furnished by the means 21 for dosing lime. Accordingly, the tail product after being alkalinized directly in the column is led by the pipeline 16 to the carbonation tank 23 provided by the biogas inlet 25 and the gas outlet 28.

In all three embodiments, that of FIG. 1 and those of FIGS. 2, and 3, the carbonation can be alternatively carried out by means of carbon dioxide obtained as one fraction of the gaseous phase leaving the distillation column 11 through the pipe 15. The respective branch of the pipe 15 connected to the carbonation tank 20a or 23 and applicable if carbon dioxide obtained by distillation were used as the carbonation medium is identified in FIGS. 2 and 3 by a dash line 15a.

In the embodiments wherein alkalization proceeds outside the distillation column 11, (FIGS. 1 and 2) it is possible to accelerate that operation by the additional supply of heat, advantageously in the form of hot steam. The supply line of steam 34 is identified by dash line 34 in FIGS. 2 and 3.

Although the invention is illustrated and described with reference to one preferred embodiment thereof, it is to be expressly understood that it is in no way limited to the disclosure of such preferred embodiment but is capable of numerous modifications within the scope of the appended claims.

We claim:

1. A method of producing concentrated nitrogen compounds, phosphate containing concentrate and clear water from a liquid component obtained after anaerobic digestion of organic compounds in waste waters containing nitrogen in the form of ammonium salts of carbonic acid comprising the sequential steps of:
   (a) heating the liquid component to a boiling temperature;
   (b) subjecting the heated liquid component to a rectification thereby producing gaseous fractions of ammonia, carbon dioxide and water, and a tail fraction;
   (c) isolating the gaseous fractions separately or as compounds formed by their chemical reaction as ammonium carbonate and ammonium water, and isolating the tail fraction with the residual content of less than 200 mg $NH_3$ bonded as ammonium salts thereto per 1 kg of the tail fraction;
   (d) alkalizing the tail fraction by adding an equivalent of lime up to 20 g CaO per 1 kg at a temperature of 60° to 100° C., while simultaneously draining any residual ammonia;
   (e) carbonating with carbon dioxide the alkalized product to a final value of 0.01 to 1.5 g CaO per 1 kg; and
   (f) separating an organo-phosphate-lime concentrate and clear water.

2. The method according to claim 1, wherein biogas from the anaerobic digestion is used for carbonation.

3. The method according to claim 1, wherein carbon dioxide obtained by rectification of the liquid component is used for carbonation.

4. The method according to claim 1, wherein the liquid component in rectification is heated by heat obtained by combusting of biogas from anaerobic digestion.

5. The method according to claim 1, wherein the liquid component to be rectified is preheated by the heat of clear water separated in a decanter.

6. The method according to claim 1, wherein the liquid component to be rectified is preheated by the heat of clear water obtained after separating the organo-phosphato-lime and clear water.

7. The method according to claim 1, wherein the liquid component from the anaerobic digestion is preheated by a heat accumulated in the tail fraction of the rectification.

* * * * *